United States Patent
Szczepanski

(10) Patent No.: US 10,287,958 B2
(45) Date of Patent: May 14, 2019

(54) SUBSTRATE AND FILTER WITH STRESS/STRAIN DETECTION AND METHOD OF USE

(71) Applicant: Denso International America, Inc., Southfield, MI (US)

(72) Inventor: Edward Szczepanski, Grosse Pointe Woods, MI (US)

(73) Assignee: DENSO International America, Inc., Southfield, MI (US)

( * ) Notice: Subject to any disclaimer, the term of this patent is extended or adjusted under 35 U.S.C. 154(b) by 220 days.

(21) Appl. No.: 15/384,805

(22) Filed: Dec. 20, 2016

(65) Prior Publication Data

US 2018/0171854 A1 Jun. 21, 2018

(51) Int. Cl.
| | | |
|---|---|---|
| F01N 11/00 | (2006.01) | |
| G01B 21/32 | (2006.01) | |
| G01N 25/00 | (2006.01) | |
| G01N 27/04 | (2006.01) | |

(52) U.S. Cl.
CPC .......... *F01N 11/00* (2013.01); *F01N 2550/02* (2013.01); *F01N 2560/12* (2013.01); *F01N 2900/16* (2013.01); *G01B 21/32* (2013.01); *G01N 25/00* (2013.01); *G01N 27/04* (2013.01); *Y02T 10/47* (2013.01)

(58) Field of Classification Search
CPC ..... F01N 11/00; F01N 2550/02; G01N 27/04; G01N 25/00; G01B 21/32
See application file for complete search history.

(56) References Cited

U.S. PATENT DOCUMENTS

| | | | | |
|---|---|---|---|---|
| 5,339,628 A | * | 8/1994 | Maus ........................ | F01N 9/00 374/E7.021 |
| 5,560,200 A | * | 10/1996 | Maus .................... | F01N 11/002 60/274 |
| 5,758,492 A | * | 6/1998 | Kato ...................... | F01N 3/2013 219/497 |
| 7,815,370 B2 | * | 10/2010 | Simon, III ............ | F01N 11/002 116/207 |
| 7,886,523 B1 | * | 2/2011 | Legare .................. | F02D 41/008 60/274 |
| 8,298,293 B2 | * | 10/2012 | Leydet ...................... | A61F 2/68 623/24 |
| 8,984,861 B2 | * | 3/2015 | Sakamoto ............... | F01N 11/00 60/274 |
| 9,200,552 B2 | * | 12/2015 | Hirai ...................... | F01N 3/101 |
| 9,206,728 B2 | * | 12/2015 | Tanaka .................... | F01N 11/00 |
| 9,347,353 B2 | * | 5/2016 | Yoshioka .............. | F01N 3/2013 |
| 2006/0156794 A1 | | 7/2006 | Horn et al. | |
| 2007/0255424 A1 | * | 11/2007 | Leydet ...................... | A61F 2/68 623/24 |
| 2012/0260638 A1 | * | 10/2012 | Yoshioka .............. | F01N 3/2013 60/295 |
| 2013/0025267 A1 | * | 1/2013 | Yoshioka .............. | F01N 3/2026 60/300 |
| 2014/0292350 A1 | * | 10/2014 | Yoshioka .............. | F01N 3/2013 324/551 |

\* cited by examiner

*Primary Examiner* — Freddie Kirkland, III

(74) *Attorney, Agent, or Firm* — Harness, Dickey & Pierce, P.L.C.

(57) ABSTRACT

A catalytic converter includes a cylindrical catalyst substrate and a detection device monitoring the integrity of the catalyst substrate. The detection device monitoring the integrity of the catalyst substrate is a band formed on an outer circumference of the catalyst substrate.

20 Claims, 7 Drawing Sheets

SUBSTRATE AND FILTER WITH STRESS/STRAIN DETECTION AND METHOD OF USE

FIELD

The present disclosure relates to catalytic converters and, specifically, a device and method for monitoring the integrity of a catalyst substrate within a catalytic converter.

BACKGROUND

This section provides background information related to the present disclosure which is not necessarily prior art.

Often, when a vehicle is brought into a dealer for a rattle or noise coming from a catalytic converter, a dealership technician will remove the catalytic converter and send it to the supplier for examination without determining whether the catalytic converter is actually malfunctioning or whether a catalyst substrate within the catalytic converter is damaged. Currently, there is no tool that assists the dealership technician in diagnosing the rattle or noise. The dealership technician simply warranties the parts and replaces the entire exhaust system and catalytic converter. Replacing the entire exhaust system and catalytic converter can be very expensive and lead to unnecessary increased warranty costs for the parent company. Thus, there is a need for an integrated device associated with the catalytic converter which can verify whether the catalyst substrate is compromised or cracked.

Additionally, during the design phase of the catalytic converter, the design engineer or test technician wraps pressure paper around the catalyst substrate and makes a guess at a pressure at which to test the catalyst substrate. When the part is removed from the pressure paper, the color of the paper tells only the maximum pressure applied to the catalyst substrate. The maximum pressure, or color of the paper, is determined based on visual inspection by the design engineer or test technician and is therefore subjective and could change from person to person. Further, the entire process of wrapping the catalyst substrate, applying the pressure, unwrapping the catalyst substrate, and visually inspecting the paper is time consuming. Thus, there is a need for a device that can accurately indicate the stress on a catalyst substrate in real time to quicken the matting strategy process and reduce the cost of materials.

SUMMARY

This section provides a general summary of the disclosure, and is not a comprehensive disclosure of its full scope or all of its features.

A catalytic converter includes a cylindrical catalyst substrate and a detection device monitoring the integrity of the catalyst substrate. The detection device monitoring the integrity of the catalyst substrate is a band formed on an outer circumference of the catalyst substrate.

The catalytic converter may further include a detection device that provides readings indicating stress or strain caused by expansion or compression of the catalyst substrate.

The catalytic converter may further include a detection device having a positive terminal, a negative terminal, and a wire connecting the positive terminal to the negative terminal. The detection device may be configured to provide a resistance measurement of a current flowing through the wire.

The catalytic converter may further include a plurality of detection devices that are disposed around the outer circumference of the catalyst substrate. A first of the plurality of detection devices may be disposed near a first end of the catalyst substrate. A second of the plurality of detection devices may be disposed in a center of the catalyst substrate. A third of the plurality of detection devices may be disposed near a second end of the catalyst substrate. Each of the plurality of detection devices provides a resistance measurement of a current flowing through the detection device.

The catalytic converter may further include a detection device that provides a resistance measurement indicating a temperature of the catalyst substrate at a location of the detection device on the catalyst substrate.

The catalytic converter may further include a detection device that is a strain gauge.

The catalytic converter may further include a detection device that is a single band of a plurality of strain gauges connected in series.

The catalytic converter may further include a detection device that is a single band of a plurality of strain gauges connected in parallel.

The catalytic converter may further include a detection device that is a band of conductive material connecting a positive end with a negative end and having an electrical current flowing therethrough.

The catalytic converter may further include a detection device that is embedded into or onto the catalyst substrate using three-dimensional printing.

The catalytic converter may further include a detection device that is circuit printed onto the catalyst substrate.

The catalytic converter may further include a detection device that is adhered onto the catalyst substrate.

A vehicle includes a catalyst substrate, a detection device, and a controller. The detection device is configured to provide a signal monitoring the integrity of the catalyst substrate. The controller receives the signal from the detection device and determines a stress or strain on the catalyst substrate or a fracture in the catalyst substrate. If the controller determines that there is a fracture in the catalyst substrate, the controller stores the time of the fracture and the stress or strain measurements and provides a signal indicating that the catalyst substrate has been compromised.

The vehicle may further include a detection device having a positive terminal, a negative terminal, and a conductive band connecting the positive terminal to the negative terminal. The detection device may be configured to provide a resistance measurement of a current flowing through the conductive band.

The vehicle may further include a controller that determines the stress or strain on the catalyst substrate from a resistance measurement of the current flowing through the conductive band and determines the fracture in the catalyst substrate from an interruption in current flowing through the conductive band.

A method for monitoring an integrity of a catalyst substrate includes providing a signal, by a detection device, indicating a resistance measurement of a current flowing through a circuit in the detection device; determining, by a controller or a device monitor, whether the circuit is complete; signaling, by the controller or the device monitor, a catalyst substrate failure if the circuit is not complete; and reporting, by the controller or the device monitor, a stress or strain measurement and a time for the catalyst substrate failure if the circuit is not complete.

The method may further include use of a detection device that is disposed around an outer circumference of the catalyst substrate.

The method may further include connecting the device monitor to the detection device; wrapping the catalyst substrate with a mat insulation; placing the catalyst substrate and mat insulation within a canning sleeve; and placing the canning sleeve under a first reduced diameter or a first stress level. The device monitor may determine whether the circuit is complete after the canning sleeve is placed under the first reduced diameter or the first stress level.

The method may further include reporting, by the device monitor, a stress or strain measurement for the catalyst substrate failure if the device monitor determines that the circuit in the detection device is complete; and placing the canning sleeve under an increased reduced diameter or an increased first stress level if the device monitor determines that the circuit in the detection device is complete.

The method may further include continuing to provide a signal, by the detection device, indicating the resistance measurement of the current flowing through the circuit in the detection device if the controller determines that the circuit in the detection device is complete.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present teachings advantageously provide a device and method for determining an appropriate canning pressure for a catalytic canister during the design process and for monitoring catalyst canisters in an exhaust system of a vehicle. The stress/strain detection device and method will assist a dealership technician in diagnosing rattles, noises, and failures in the exhaust system and will decrease warranty costs seen by the parent company for unnecessarily warrantying exhaust systems and catalytic converters. Further, the stress/strain detection device and method will assist the design engineer in the investigation of the type and quantity of matting material to wrap around a catalyst converter and will decrease the test time and material cost by eliminating the need for pressure paper during the process.

Figure 1:
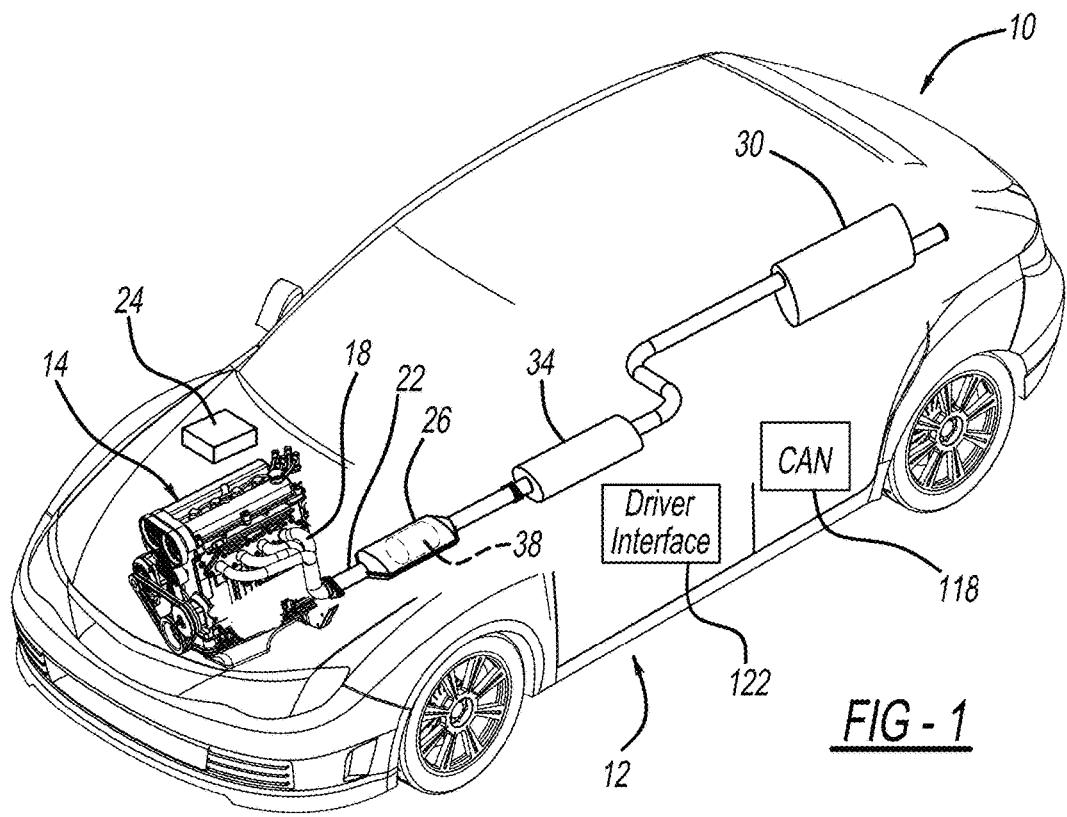
FIG. 1 is a vehicle including a catalytic converter having a catalyst substrate according to the present teachings.

With reference to FIG. 1, a vehicle 10 including a stress/strain detection device 70 (FIGS. 3A-6) and system 12 according to the present teachings is illustrated. Although the vehicle 10 is illustrated as an automobile in FIG. 1, the present teachings apply to any other suitable vehicle, such as a sport utility vehicle (SUV), a mass transit vehicle (such as a bus), or a military vehicle, as examples. The vehicle 10 further includes an engine 14 having an exhaust manifold 18 out of which one or more exhaust pipes 22 extend and a controller, or control module, 24 controlling the functions of the engine 14. A catalytic converter, or catalyst, 26 and a muffler 30 may be disposed along each of the one or more exhaust pipes 22. Additional exhaust parts 34 such as a resonator, a performance mid-pipe muffler, a diesel oxidation catalyst, or a particulate filter (depending on the type of vehicle) may also be disposed along the exhaust pipe 22.

The catalytic converter 26 reduces the toxicity of emissions from the engine 14. The catalytic converter 26 may be a three-way catalytic converter, a two-way catalytic converter, an oxidation catalyst, an NOx adsorber catalyst, a diesel particulate filter, a diesel oxidation catalyst, or any other type of catalytic converter. A three-way catalytic converter performs three simultaneous tasks: (1) reduction of nitrogen oxides to nitrogen and oxygen ($2NO_x \rightarrow xO_2 + N$), (2) oxidation of carbon monoxide to carbon dioxide ($2CO + O_2 \rightarrow 2CO_2$), and (3) oxidation of unburnt hydrocarbons (HC) to carbon dioxide and water $$\left(C_xH_{2x+2} + \left[\frac{3x+1}{2}\right]O_2 \rightarrow xCO_2 + (x+1)H_2O\right).$$

A two-way catalytic converter performs two simultaneous tasks: (1) oxidation of carbon monoxide to carbon dioxide ($2CO + O_2 \rightarrow 2CO_2$), and (2) oxidation of un-burnt and partially-burnt hydrocarbons (HC) to carbon dioxide and water $$\left(C_xH_{2x+2} + \left[\frac{3x+1}{2}\right]O_2 \rightarrow xCO_2 + (x+1)H_2O\right).$$

An oxidation catalyst converts carbon monoxide and hydrocarbons to carbon dioxide and water

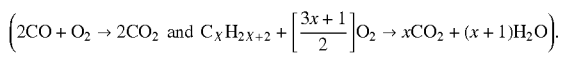

A NOx adsorber catalyst reduces NOx to N2 and eliminates stored NOx in the system ($2NO_X \rightarrow xO_2+N$). A diesel particulate filter filters diesel particulate matter (small solid particles resulting from the burning of diesel fuel containing soot, hydrocarbons, ashes, and sulphuric acid) and is periodically regenerated to burn off the particulate matter. A diesel oxidation catalyst operates as an oxidation catalyst to reduce CO and HC

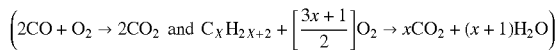

and destroy the organic fraction of the diesel particulate matter.

Figure 2:
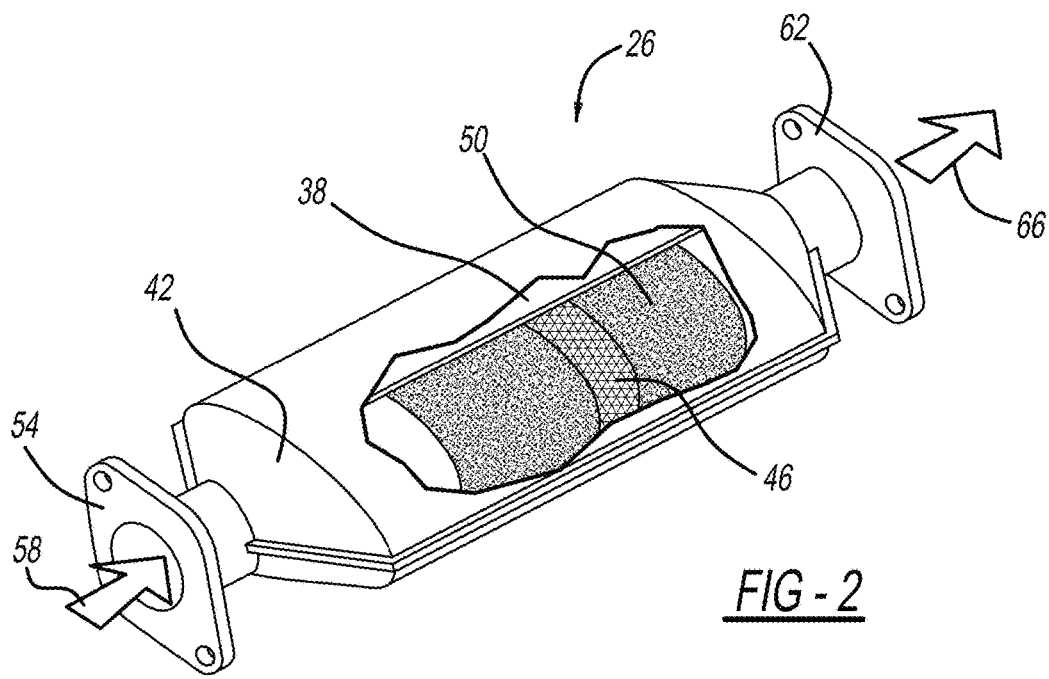
FIG. 2 is the catalytic converter of FIG. 1 with a portion of a heat shield, a catalytic converter body, and mat insulated packaging removed to show the catalyst substrate.

Referring additionally to FIG. 2, the catalytic converter 26 includes a catalyst canister body, or catalytic converter body, 38 disposed within a heat shield 42. The catalyst canister body 38 may be formed from stainless steel. A catalyst substrate, or monolith, 46 is wrapped with mat insulation packing 50 within the catalyst canister body 38. The catalyst substrate 46 may be a cylindrical substrate or a substrate with an elliptical cross-section. The catalyst substrate 46 may further have a honeycomb structure and be formed from cordierite, silicon carbide, a metal, cerium (Ce), ceramic, stainless steel, or any other appropriate material. The catalyst substrate 46 is coated with a thin layer of catalyst, being active material such as alumina oxide, cerum oxide, and rare earth stabilizer metals such as platinum (Pt), palladium (Pd), and rhodium (Rh). In other embodiments, gold (Au), cerium (Ce), iron (Fe), manganese (Mn), and nickel (Ni) may also be used. The mat insulation packing 50 insulates, seals, and provides an enclosure for the catalyst substrate 46. The structure and density of the mat insulation packing 50 determines the amount of insulation, sealing, and support the mat insulation packing 50 provides for the catalyst substrate 46. Examples of structures of the mat insulation packing 50 are intumescent/non-intumescent matting, ceramic fiber, wire mesh, fiber glass, or any other material that both insulates and provides support for the catalyst substrate.

During use of the catalytic converter 26, exhaust gas including hydrocarbons (HC), carbon monoxide (CO) and nitrogen oxide (NOx) enters a front end 54 of the catalytic converter 26 at the arrow 58. As the exhaust gas passes through the honeycomb structure of the catalyst substrate 46 a chemical reaction occurs between the hydrocarbons (HC), carbon monoxide (CO) and nitrogen oxide (NOx) in the exhaust gas and the catalytic active material to reduce and/or oxidize the harmful gasses as previously described. Tail pipe emissions including water (H20), carbon dioxide (CO2), and nitrogen (N2) then exit the catalytic converter 26 at a rear end 62 at arrow 66.

Figure 3A:
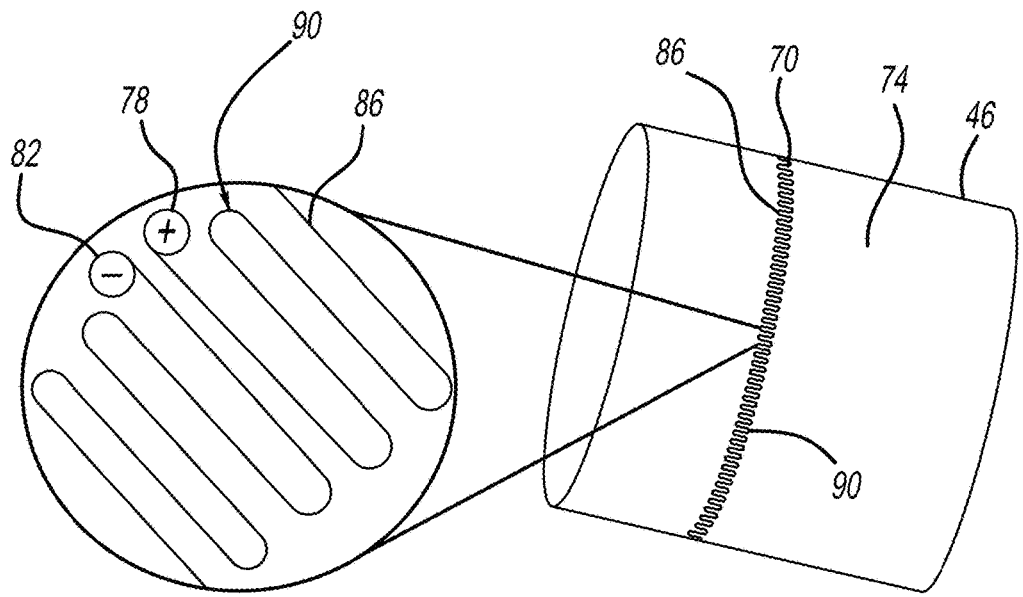
FIG. 3A is a catalyst substrate including a stress/strain detection device according to the present teachings.
Figure 3B:
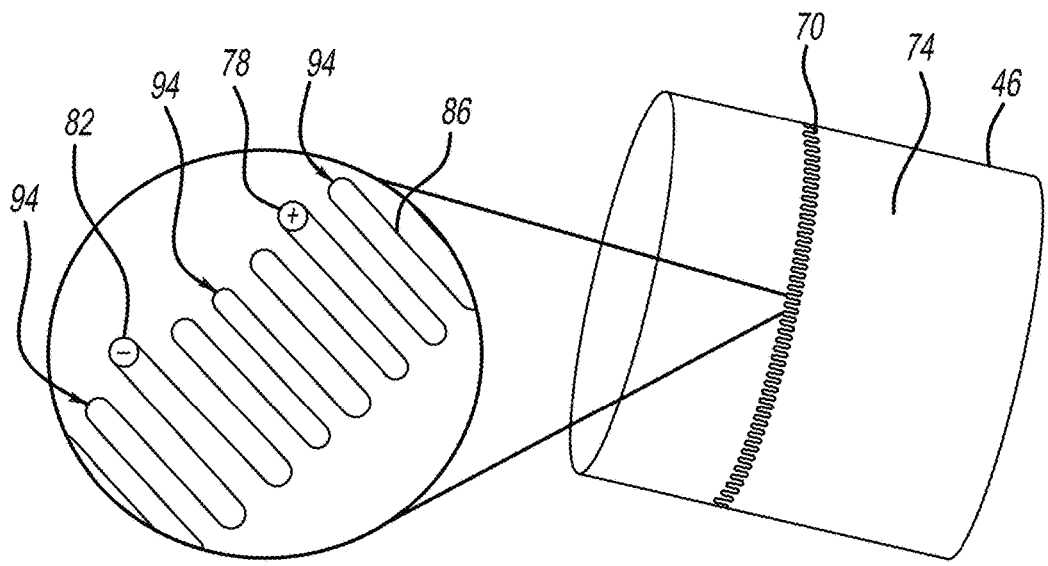
FIG. 3B is a catalyst substrate having another stress/strain detection device according to the present teachings.

Now referring to FIGS. 3A and 3B, the stress/strain detection device 70 may be disposed on the catalyst substrate 46 to measure stress or strain caused by expansion or compression of the catalyst substrate 46 and perform continuous monitoring of the catalyst substrate 46 when the catalyst substrate 46 is installed in the vehicle 10. In some embodiments, the stress/strain detection device 70 may be a strain gauge disposed in a band around an external surface 74 of the catalyst substrate 46. A strain gauge is a sensor whose resistance varies with applied force. The strain gauge converts force, pressure, tension, weight, etc., into a change in electrical resistance which can be measured (further described below). Although a strain gauge is discussed in the present teachings, any conductive material that would be severed in the event of a fracture of the catalyst substrate 46 may be used.

The stress/strain detection device 70 may include a positive terminal 78 and a negative terminal 82 with a wire 86 disposed therebetween. While the wire 86 is illustrated as being disposed in a zig-zag or sinusoidal pattern, the wire may be disposed in a square wave, a straight band or any other pattern around the external surface 74 of the catalyst substrate 46.

In some embodiments, as shown in FIG. 3A, the stress/strain detection device 70 may be formed as a single continuous band 90 of wire 86 around the external surface 74 of the catalyst substrate 46. In other embodiments, as shown in FIG. 3B, the stress/strain detection device 70 may be comprised of a series of multiple stress/strain detection devices 94 connected in series or parallel.

The stress/strain detection device 70 may be printed onto, embedded into, or embedded onto the catalyst substrate 46. Three-dimensional (3D) printing technology or circuit printing may be used to fix the stress/strain detection device 70 onto the external surface 74 or within the external surface 74 of the catalyst substrate 46. Additionally, the stress/strain detection device 70 may be applied or adhered onto the external surface 74 of the catalyst substrate 46 by an adhesive. Thus, new catalyst substrates 46 may be manufactured with the stress/strain detection device 70 and pre-existing catalyst substrates 46 may be retrofitted with the stress/strain detection device 70.

Figure 4A:
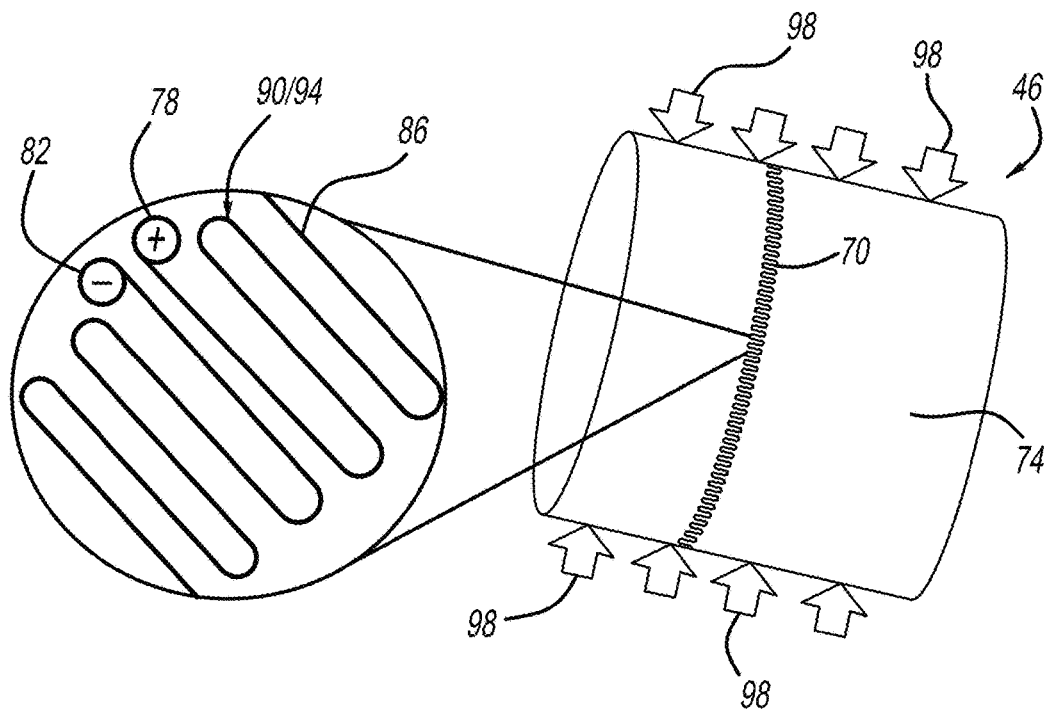
FIG. 4A is a catalyst substrate having a stress/strain detection device according to the present teachings, where the catalyst canister is subject to compressive forces.

Now referring to FIG. 4A, during design, the catalyst substrate 46 is compressed to help determine the type and amount of mat insulation packing 50 necessary for the catalytic converter 26. During use, the catalyst substrate 46 may be subjected to compressive forces due to temperature increase. During production, the catalyst substrate 46 may be subjected to compressive forces applied to the converter body 38 and mat insulation packaging 50 to retain the catalyst substrate 46 in an assembly position. When the catalyst substrate 46 is compressed, or when compressive forces act on the exterior surface 74 of the catalyst substrate 46 (shown by arrows 98), the wire 86 between terminals 78, 82 of the stress/strain detection device 70 thickens or increases in diameter, causing a lower resistance condition. The thickening of the wire 86 decreases the resistance to electrical current that flows from the positive terminal 78 to the negative terminal 82 through the wire 86. The strain on the catalyst substrate 46 is measured by the resistance decrease. For example, the ratio of relative change in electrical resistance R to the mechanical strain c, or gauge factor (strain factor), may be calculated as:

$$GF = \frac{\frac{\Delta R}{R}}{\varepsilon} = \frac{\frac{\Delta \rho}{\rho}}{\varepsilon} + 1 + 2v$$

where $\varepsilon$ is mechanical strain which is equal to $\Delta L/L_0$, $\Delta L$ is the absolute change in length, $L_0$ is the original length, v is Poisson's ratio, $\Delta \rho$ is change in resistivity, $\rho$ is unstrained resistivity, $\Delta R$ is change in strain gauge resistance, and R is unstrained resistance of strain gauge.

Figure 4B:
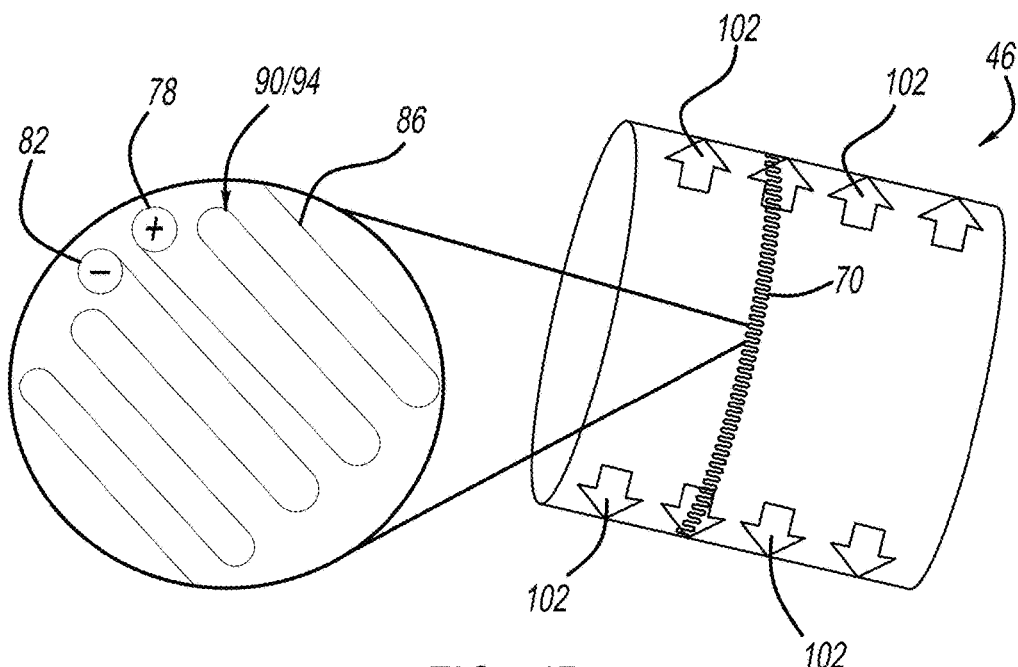
FIG. 4B is a catalyst substrate having a stress/strain detection device according to the present teachings, where the catalyst canister is subject to expansive forces.

Referring to FIG. 4B, during design, the catalyst substrate 46 may also be subjected to expansive forces to help determine the type and amount of mat insulation packing 50 necessary for the catalytic converter 26. During use, the catalyst substrate 46 may be subjected to expansive forces due to temperature decrease. When the catalyst substrate 46 expands, or when expansive forces act on the catalyst substrate 46 (shown by arrows 102), the wire 86 between terminals 78, 82 of the stress/strain detection device 70 thins or decreases in diameter, causing a high resistance condition. The thinning of the wire 86 increases the resistance to the electrical current that flows from the positive terminal 78 to the negative terminal 82 through the wire 86. The strain on the catalyst substrate 46 is measured by the resistance increase. For example, the gauge factor (strain factor) equation, previously described, may be used to calculate the strain on the catalyst substrate 46.

Figure 4C:
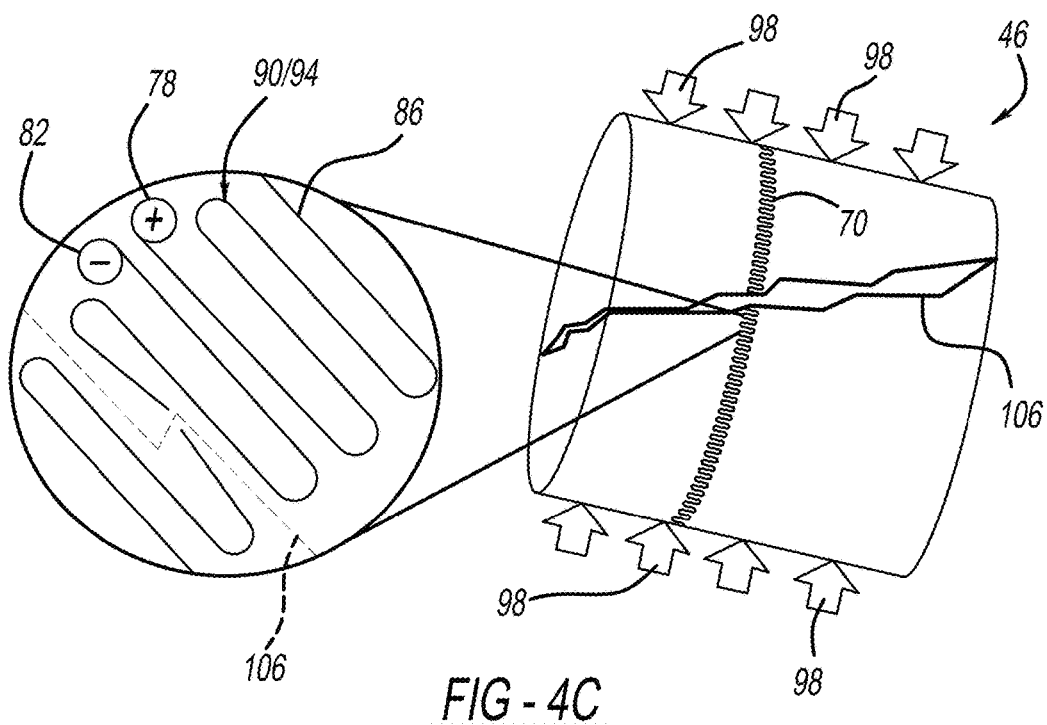
FIG. 4C is a catalyst substrate having a stress/strain detection device according to the present teachings, where the catalyst canister has been compromised or fractured.

Referring to FIG. 4C, and in light of the descriptions of FIGS. 4A and 4B, when a catalyst substrate 46 is subjected to either compressive or expansive forces 98, 102 in excess, the catalyst substrate 46 will become compromised by a fracture or failure. For example, a failure due to excessive compressive force 98 on the catalyst substrate 46 is illustrated in FIG. 4C. The threshold at which the catalyst substrate 46 is compromised may depend on the material, structure, and dimensions of the substrate and external factors such as temperature.

During a failure, the catalyst substrate 46 cracks or separates as shown by a fracture 106 in FIG. 4C. The fracture 106 penetrates through the wire 86 of the stress/strain detection device 70, separating the wire 86 and causing a break in the electrical current flowing from the positive terminal 78 to the negative terminal 82. Although the fracture 106 is illustrated as a result of excessive compressive force 98 in FIG. 4C, the same result will occur with an excess in the expansive forces 102 (FIG. 4B) previously discussed.

Figure 5:
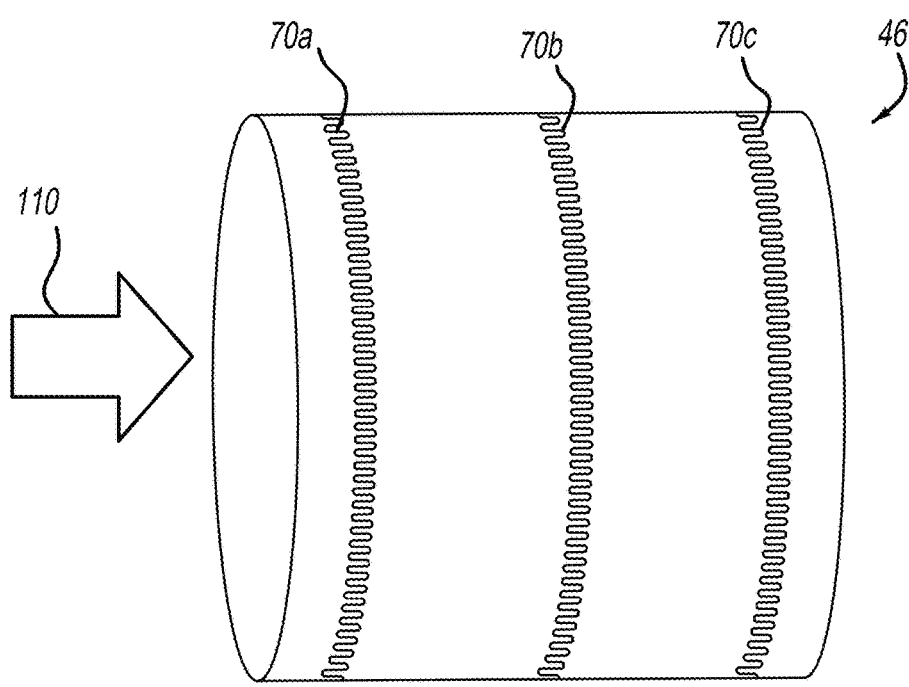
FIG. 5 is a catalyst substrate having stress/strain detection devices according to the present teachings disposed in the front, center, and rear of the catalyst canister to detect temperature behavior of the catalyst.

Now referring to FIG. 5, multiple stress/strain detection devices 70a, 70b, 70c may be disposed on the catalyst substrate 46. While three stress/strain detection devices 70a, 70b, 70c are illustrated and discussed, it is understood that any number of stress/strain detection devices may be used and placed in any location on the catalyst substrate 46. Multiple bands of the stress/strain device 70a, 70b, 70c determine and monitor the temperature and thermal behavior of the catalyst substrate 46 in real time by providing the differences in strain between the multiple stress/strain devices 70a, 70b, 70c. By placing a stress/strain detection device 70a at a first end, a stress/strain detection device 70b at a center, and a stress/strain detection device 70c at a second end, a catalyst temperature or temperature behavior of the catalyst substrate 46 may be monitored. The temperature at each location, or the thermal behavior of the catalyst substrate 46, can be monitored by catalyst thermal expansion (i.e., expansive forces 102) or compression (i.e., compressive forces 98).

For example, hot exhaust gas, or heat, flows through the catalyst substrate 46 as indicated at arrow 110. The resistance of current through the circuit in each of the stress/strain detection devices 70a, 70b, 70c, can determine the temperature at the respective locations of the stress/strain detection devices 70a, 70b, 70c. For example, as the temperature of the catalyst substrate 46 increases, the catalyst substrate 46 undergoes thermal expansion (similar to the illustration in FIG. 4B). Thus, the wire 86 between terminals 78, 82 of the stress/strain detection device 70 thins or decreases in diameter, causing a high resistance condition. The thinning of the wire 86 increases the resistance to the electrical current that flows from the positive terminal 78 to the negative terminal 82 through the wire 86. The strain (and therefore the temperature) on the catalyst substrate 46 is measured by the resistance increase (using the gauge factor/strain factor equation previously described). The higher the temperature of the catalyst substrate 46, the thinner the wire 86 between terminals 78, 82.

Using the stress/strain detection devices 70a, 70b, 70c to determine the temperatures at various locations on the catalyst substrate 46 is beneficial for determining how quickly the catalyst substrate 46 heats up from front to rear during vehicle 10 start-up. Knowing the time for the catalyst substrate 46 to heat up effects the catalyst light off duration and vehicle emissions at start-up. Further, temperature differences in the stress/strain detection devices 70a, 70b, 70c could indicate the location of one or more cracks in the catalyst substrate 46.

By utilizing the configurations described in relation to FIGS. 3A-5, the catalyst substrate 46 may be continuously monitored. Continuous monitoring of the catalyst substrate is very beneficial in verifying the integrity of the catalyst substrate, troubleshooting issues with the catalyst substrate, and monitoring temperatures of the catalyst substrate. Continuous monitoring of the catalyst substrate 46 provides engine conditions at the exact point of a catalyst substrate 46 failure which can be used to diagnose other issues in the vehicle 10 system. The stress/strain detection device 70 will provide the time of the failure and the stress and/or strain (and thus temperature) on the catalyst substrate 46 at the time of the failure. The time of the failure may then be used to gather specific engine (and other) data.

Continuous monitoring of the catalyst substrate 46 further provides an indication of how the catalyst substrate 46 is handling extreme cold starts (for example only, less than or equal to 30 degrees Celsius). As previously stated, using multiple stress/strain detection devices 70a, 70b, 70c to monitor (and record) the temperatures at various locations on the catalyst substrate 46 is beneficial for determining how quickly the catalyst substrate 46 heats up from front to rear at start-up, which effects the catalyst light off duration and vehicle emissions at start-up. The conditions for catalyst light off and performing vehicle emissions diagnostics during extreme cold starts can be stressful on the catalyst substrate 46. Therefore, continuous monitoring of the catalyst substrate 46 can provide a constant check on the integrity of the catalyst substrate 46.

Figure 6:
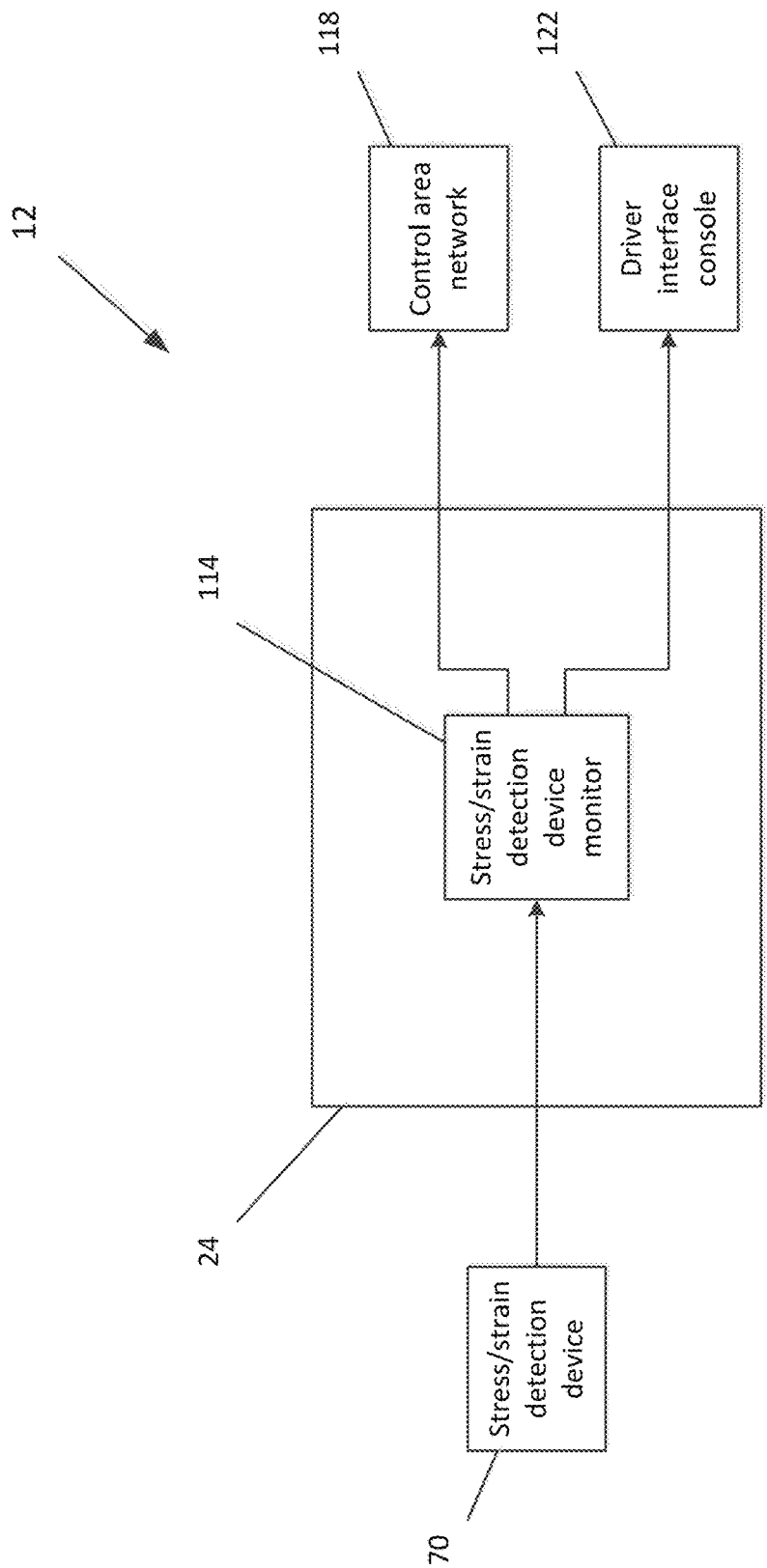
FIG. 6 is a block diagram of a system according to the present teachings for detecting a stress and/or strain on a catalyst substrate and determining when a catalyst substrate has been compromised.

With reference to FIG. 6, a block diagram of the stress/strain detection system 12 according to the present teachings for the stress/strain detection device 70 is shown. The stress/strain detection device 70 communicates with a stress/strain detection device monitor 114 in the control module 24 in the vehicle 10. The stress/strain detection device monitor 114 receives signals from the stress/strain detection device 70 indicating a resistance on the current flowing through the wire 86 connecting the positive terminal 78 with the negative terminal 82. The stress/strain detection device monitor 114 also receives signals from the stress/strain detection device 70 indicating an interruption of flow in the electrical current.

The stress/strain detection device monitor 114 uses the data received from the stress/strain detection device 70 to determine a stress or strain on the catalyst substrate 46, a temperature of the catalyst substrate 46 in the one or more locations of the stress/strain detection device 70, and whether a failure has occurred in the catalyst substrate 46. The stress/strain detection device monitor 114 may utilize the gauge factor (strain factor) equation, as previously discussed, to determine the stress or strain on the catalyst substrate 46. The stress/strain detection device monitor 114 may determine the temperature of the catalyst substrate 46 at the location of the stress/strain detection device 70 by the resistance (due to heat) in the wire 86 of the stress/strain detection device 70, and the stress/strain detection device monitor 114 may determine that a failure has occurred in the catalyst substrate 46 if the stress/strain detection device 70 provides a signal indicating an interruption of flow in the electrical current.

The stress/strain detection device monitor 114 may further communicate with a control area network (CAN) 118 and/or a driver interface console (DIC) 122 to communicate data and/or issues with a driver or technician. The stress/strain detection device monitor 114 may record and store stress/strain measurements on the catalyst substrate 46 and temperatures of the catalyst substrate 46 for retrieval by the technician through the CAN 118. If the stress/strain detection device monitor 114 determines that a failure has occurred in the catalyst substrate 46, the stress/strain detection device monitor 114 may communicate with the DIC 122 to communicate the failure to the driver. The failure may be communicated through a light or sound, for example by illuminating a check engine light and/or sounding an alarm. The stress/strain detection device monitor 114 may also identify and store the catalyst substrate 46 conditions at the time of failure for communication to the technician through the CAN 118.

Figure 7:
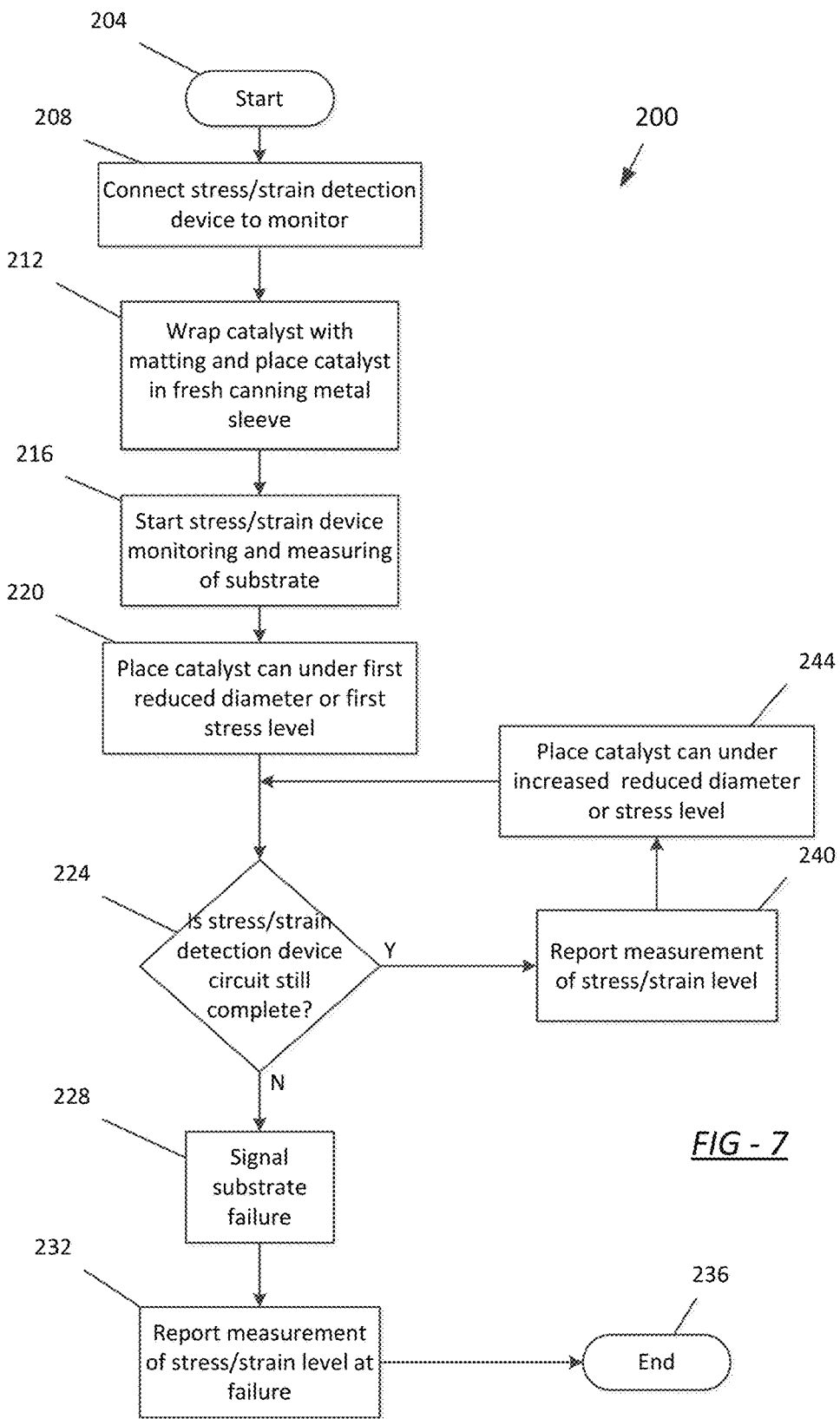
FIG. 7 is a flow diagram for a method according to the present teachings for investigating a canning pressure for the catalyst substrate during the design process.

Now referring to FIG. 7, a flowchart for a method 200 is shown. The method 200 is configured to investigate a canning pressure for the catalyst substrate 46 using the stress/strain detection device 70. The method 200 can be performed by a user or test administrator in combination with the stress/strain detection device 70 and a computer or monitoring device. The method 200 starts at 204.

At 208, at least one stress/strain detection device 70 (70a, 70b, 70c) on the catalyst substrate 46 is connected to a computer or other monitoring device to collect real time data from the stress/strain detection device 70. The computer or other monitoring device performs the same functions as the stress/strain detection device monitor 114 in the control module 24 in the vehicle 10. For example, the computer or monitoring device receives signals from the stress/strain detection device 70 indicating a resistance on the current flowing through the wire 86 connecting the positive terminal 78 with the negative terminal 82 and indicating an interruption of flow in the electrical current. The computer or monitoring device then uses the data received from the stress/strain detection device 70 to determine a stress or strain on the catalyst substrate 46, a temperature of the catalyst substrate 46 in the one or more locations of the stress/strain detection device 70, and whether a failure has occurred in the catalyst substrate 46.

At 212, the catalyst substrate 46 is wrapped with the mat insulation packaging 50 and placed in a canning metal sleeve, or catalyst canister body 38. The monitoring device begins receiving signals and/or readings from the stress/strain detection device 70 to begin monitoring or measuring the catalyst substrate 46 at 216. At 220, the canning metal sleeve, or catalyst canister body 38, is placed under a first reduced diameter or a first stress level. An example of a first reduced diameter is a reduction in diameter of the canning metal sleeve (or catalyst canister body 38) by a range of 0.1 to 10.0 percent (%). An example of a first stress level is within the range of 0.5 and 2.0 megapascals (MPa). Please note that the first reduced diameter and the first stress level may be any value that either reduces the diameter of, or applies stress to, the canning metal sleeve (or catalyst canister body 38) and may be set by the manufacturer and may vary from part to part or manufacturer to manufacturer.

At 224, the method 200 determines whether the stress/strain detection device 70 circuit is still complete. The stress/strain detection device 70 circuit is the electric circuit extending along the wire or conductive band 86 from the positive terminal 78 to the negative terminal 82. If the stress/strain detection device 70 circuit (or wire 86) has been compromised, the stress/strain detection device 70 will send a signal to the computer or monitoring device indicating an interruption of flow in the electrical current. If the stress/strain detection device 70 has not been compromised, the stress/strain detection device 70 will continue sending signals and/or readings indicating a resistance on the current flowing through the wire 86 connecting the positive terminal 78 with the negative terminal 82 (as in 216).

If the stress/strain detection device 70 circuit has been compromised at 224, a substrate failure is signaled by the computer or monitoring device at 228. This is similar to the stress/strain detection device monitor 114 communicating with the DIC 122 to communicate the failure to the driver, as previously described. At 232, the stress/strain level during the failure is reported by the computer or monitoring device and the method ends at 236.

If the stress/strain detection device 70 continues to send signals and/or readings indicating a resistance on the current flowing through the wire 86 connecting the positive terminal 78 with the negative terminal 82 at 224 (indicating that the stress/strain detection device circuit is still complete), the stress/strain level measurement is reported by the computer or monitoring device at 240. The canning metal sleeve (or catalyst canister body 38) is then placed under an increased reduced diameter or an increased stress level at 244. An example of the increased reduced diameter is an additional reduction in diameter of the canning metal sleeve (or catalyst canister body 38) by a range of 0.1 to 10.0 percent (%). An example of the increased stress level is an increase in the stress level within the range of 0.5 to 2.0 megapascals (MPa). Please note that the increased reduced diameter and the increased stress level may be any value that either further reduces the diameter of, or applies additional stress to, the canning metal sleeve (or catalyst canister body 38) and may be set by the manufacturer and may vary from part to part or manufacturer to manufacturer. The method 200 then returns to 224 to determine whether the stress/strain detection device 70 circuit is complete. The method continues the cycle of 224, 240, 244 until the stress/strain detection device 70 circuit is no longer complete at 224 and a substrate failure is signaled at 228. The stress/strain level during the failure is then reported by the computer or monitoring device at 232 and the method ends at 236.

The method 200 is beneficial for determining the type, material, and amount of mat insulation packaging necessary for the catalytic converter 26 during the design process. Additionally, the method 200 determines the expansion of the catalyst substrate 46 under differing loads and stress levels. Use of the stress/strain detection device 70 eliminates the need to use wrap pressure paper and, thus, improves the accuracy of the test results. When using wrap pressure paper, the test administrator determines the maximum pressure during the test by visual inspection of the wrap pressure paper, leading to variation between test administrators and less reliable results. The stress/strain detection device 70 provides real time, accurate, stress/strain data, an exact time of failure, and exact data at the time of failure. Further, use of the stress/strain detection device 70 reduces test time (because visual inspection of wrap pressure paper is not required) and reduces costs of design and development of the catalytic converter 26 (reduction of test time and materials).

Figure 8:
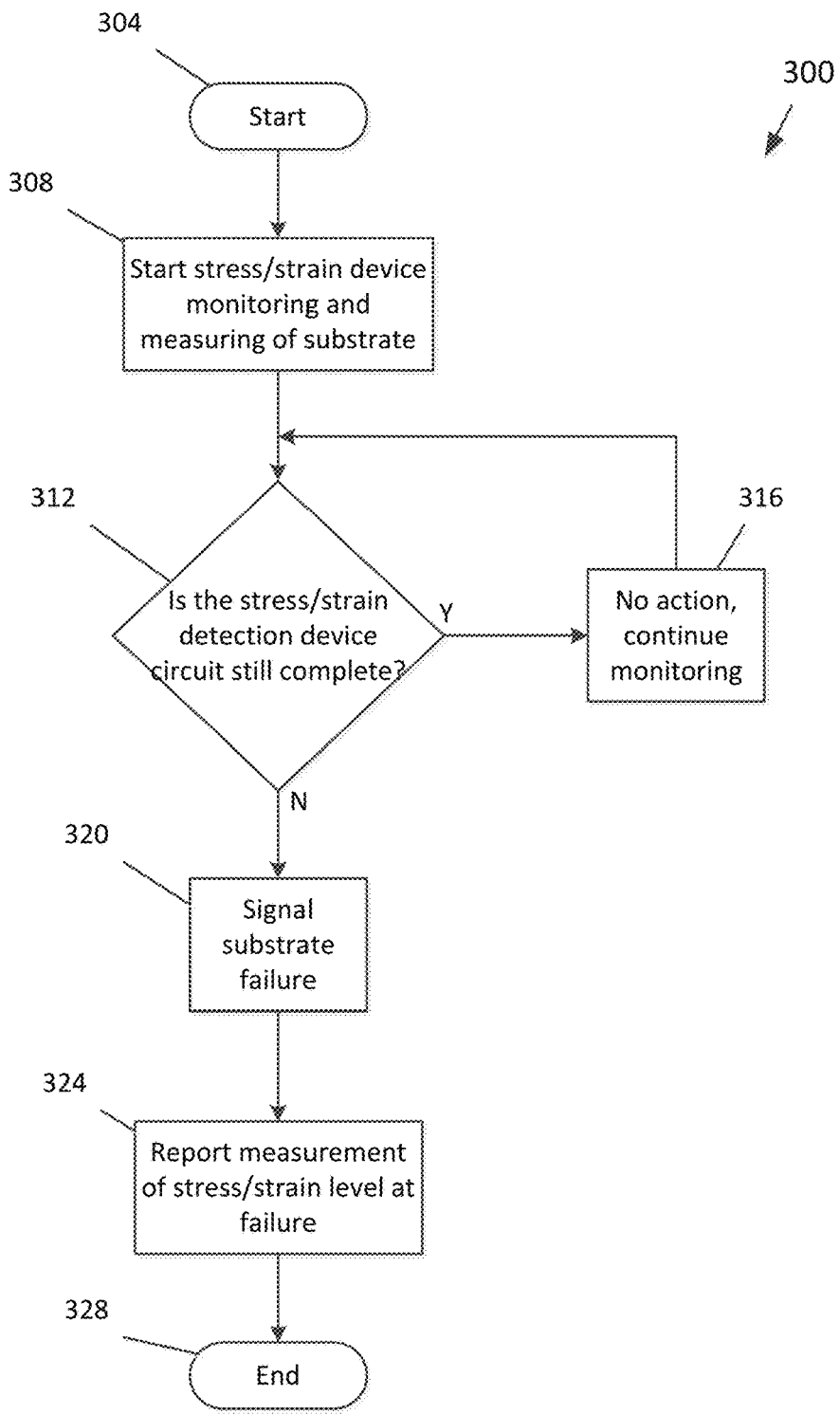
FIG. 8 is a flow diagram for a method according to the present teachings for continuously monitoring a catalyst substrate on a vehicle.

Now referring to FIG. 8, a flowchart for a method 300 is shown. The method 300 is configured to utilize the stress/strain detection device 70 to monitor the catalyst substrate 46 within the catalytic converter 26 in the vehicle 10. The method 300 can be performed using the stress/strain detection device 70 and the stress/strain detection system 12 including the controller 24, the CAN 118, and the DIC 122. The method 300 starts at 304.

At 308, the stress/strain detection device 70 begins sending signals and/or readings to the stress/strain detection device monitor 114 such that the stress/strain detection device monitor 114 monitors the integrity of the catalyst substrate 46 and records measurements of stress and/or strain on the catalyst substrate 46. For example, the stress/strain detection device monitor 114 receives signals from the stress/strain detection device 70 indicating a resistance on the current flowing through the wire 86 connecting the positive terminal 78 with the negative terminal 82 and indicating an interruption of flow in the electrical current. The stress/strain detection device monitor 114 then uses the data received from the stress/strain detection device 70 to determine a stress or strain on the catalyst substrate 46, a temperature of the catalyst substrate 46 in the one or more locations of the stress/strain detection device 70, and whether a failure has occurred in the catalyst substrate 46.

At 312, the stress/strain detection device monitor 114 determines whether the wire 86 connecting the positive terminal 78 with the negative terminal 82 in the stress/strain detection device 70 is complete. If the stress/strain detection device 70 circuit (or wire 86) has been compromised, the stress/strain detection device 70 will send a signal to the stress/strain detection device monitor 114 indicating an interruption of flow in the electrical current. If the stress/strain detection device 70 has not been compromised, the stress/strain detection device 70 will continue sending signals and/or readings indicating a resistance on the current flowing through the wire 86 connecting the positive terminal 78 with the negative terminal 82.

If the wire 86 connecting the positive terminal 78 with the negative terminal 82 in the stress/strain detection device 70 is complete at 312, the method 300 takes no action and continues monitoring the stress/strain detection device 70 at 316. The stress/strain detection device monitor 114 continues the cycle of monitoring the stress/strain detection device 70 (at 316) and determining whether the wire 86 connecting the positive terminal 78 with the negative terminal 82 in the stress/strain detection device 70 is complete (at 312) until the stress/strain detection device monitor 114 determines that the wire 86 is fractured and the stress/strain detection device 70 circuit is broken.

If the wire 86 connecting the positive terminal 78 with the negative terminal 82 in the stress/strain detection device 70 is not complete at 312, a catalyst substrate 46 failure is signaled at 320. If the stress/strain detection device monitor 114 determines that a failure has occurred in the catalyst substrate 46 (i.e., the wire 86 connecting the positive terminal 78 with the negative terminal 82 in the stress/strain detection device 70 is fractured or not complete), the stress/strain detection device monitor 114 may signal the catalyst substrate 46 failure by communicating with the DIC 122. The failure may be communicated to the driver or technician through a light or sound, such as illuminating a check engine light and/or sounding an alarm.

At 324, the stress/strain detection device monitor 114 reports the stress/strain level at the time of failure. The stress/strain detection device monitor 114 also identifies and stores the catalyst substrate 46 conditions at the time of failure for communication to the technician through the CAN 118. The method 300 then ends at 328.

The method 300 is beneficial for monitoring the integrity of the catalyst substrate 46 within the catalytic converter 26. Often, when a driver or technician identifies a rattle or other noise coming from the catalytic converter 26, the technician will remove and replace the catalytic converter 26 and send the replaced catalytic converter 26 back to the supplier for examination. Technicians have no way of determining issues within the catalytic converter 26 without cutting out and physically examining the catalyst substrate 46. Often, there is no issue with the catalyst substrate 46 and, thus, the cost and time associated with the removal and replacement of the catalytic converter 26 was unnecessary.

Use of the stress/strain detection device 70 and system 12 provides the technician with data indicating the integrity of the catalyst substrate 46 such that the technician does not need to invest the time in replacing the catalytic converter 26 if the catalyst substrate 46 is not compromised. Further, warranty costs are reduced by not removing and replacing catalytic converters 26 that are not damaged. Additionally, if there is a failure with the catalyst substrate 46, the stress/strain detection device 70 and system 12 provide data at the exact time of the failure such that the technician can determine if there is a bigger issue in the exhaust system.

In this way, the present teachings advantageously provide a device, system, and methods to detect stress and/or strain on the catalyst substrate 46, leading to reduced costs in both design and production, more accurate measurements, and a better catalytic converter 26.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element's or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A catalytic converter comprising:
an outer sleeve;
a cylindrical catalyst substrate, the catalyst substrate being disposed within the outer sleeve; and
a detection device monitoring an integrity of the catalyst substrate,
wherein the detection device includes a band formed on an outer circumference of the catalyst substrate within the outer sleeve.

2. The catalytic converter of claim 1, wherein the detection device provides readings indicating stress or strain caused by expansion or compression of the catalyst substrate.

3. The catalytic converter of claim 1, wherein the detection device includes a positive terminal, a negative terminal, and a wire connecting the positive terminal to the negative terminal, the detection device being configured to provide a resistance measurement of a current flowing through the wire.

4. The catalytic converter of claim 1, wherein a plurality of detection devices are disposed around the outer circumference of the catalyst substrate, a first of the plurality of detection devices being disposed near a first end of the catalyst substrate, a second of the plurality of detection devices being disposed in a center of the catalyst substrate, and a third of the plurality of detection devices being disposed near a second end of the catalyst substrate, and
wherein each of the plurality of detection devices provides a resistance measurement of a current flowing through the detection device.

5. The catalytic converter of claim 4, wherein the resistance measurement indicates a temperature of the catalyst substrate at a location of the detection device on the catalyst substrate.

6. The catalytic converter of claim 1, wherein the detection device is a strain gauge.

7. The catalytic converter of claim 1, wherein the detection device is a single band of a plurality of strain gauges connected in series.

8. The catalytic converter of claim 1, wherein the detection device is a single band of a plurality of strain gauges connected in parallel.

9. The catalytic converter of claim 1, wherein the detection device is a band of conductive material connecting a positive end with a negative end and having an electrical current flowing therethrough.

10. The catalytic converter of claim 1, wherein the detection device is embedded into or onto the catalyst substrate.

11. The catalytic converter of claim 1, wherein the detection device is circuit printed onto the catalyst substrate.

12. The catalytic converter of claim 1, wherein the detection device is adhered onto the catalyst substrate.

13. A vehicle comprising:
a catalytic converter having a catalyst substrate disposed within an outer sleeve;
a detection device disposed on an outer surface of the catalyst substrate and configured to provide a signal monitoring an integrity of the catalyst substrate; and
a controller receiving the signal from the detection device and determining a stress or strain on the catalyst substrate or a fracture in the catalyst substrate,
wherein if the controller determines that there is a fracture in the catalyst substrate, the controller stores a time of the fracture and the stress or strain measurements and provides a signal indicating that the catalyst substrate has been compromised.

14. The vehicle of claim 13, wherein the detection device includes a positive terminal, a negative terminal, and a conductive band connecting the positive terminal to the negative terminal, the detection device being configured to provide a resistance measurement of a current flowing through the conductive band.

15. The vehicle of claim 14, wherein the controller determines the stress or strain on the catalyst substrate from the resistance measurement of the current flowing through the conductive band and determines the fracture in the catalyst substrate from an interruption in current flowing through the conductive band.

16. A method for monitoring an integrity of a catalyst substrate disposed in an outer sleeve of a catalytic converter, the method comprising:
providing a signal, by a detection device disposed on an outer surface of the catalyst substrate, indicating a resistance measurement of a current flowing through a circuit in the detection device;

determining, by a controller or a device monitor, whether the circuit is complete based on the resistance measurement;

signaling, by the controller or the device monitor, a catalyst substrate failure if the circuit is not complete; and reporting, by the controller or the device monitor, a stress or strain measurement and a time for the catalyst substrate failure if the circuit is not complete.

17. The method of claim 16, wherein the detection device is disposed around an outer circumference of the catalyst substrate.

18. The method of claim 17, further comprising:

connecting the device monitor to the detection device;

placing the outer sleeve under a first reduced diameter or a first stress level, wherein the catalyst substrate is wrapped with a mat insulation and the catalyst substrate and mat insulation are disposed within the outer sleeve; and determining, by the device monitor, whether the circuit is complete after the outer sleeve is placed under the first reduced diameter or the first stress level.

19. The method of claim 18, further comprising:

reporting, by the device monitor, a stress or strain measurement for the catalyst substrate failure if the device monitor determines that the circuit in the detection device is complete; and placing the outer sleeve under an increased reduced diameter or an increased first stress level if the device monitor determines that the circuit in the detection device is complete.

20. The method of claim 16, further comprising continuing to provide a signal, by the detection device, indicating the resistance measurement of the current flowing through the circuit in the detection device if the controller determines that the circuit in the detection device is complete.

* * * * *